United States Patent [19]

Biermans et al.

[11] 4,115,449
[45] Sep. 19, 1978

[54] PROCESS FOR PREPARING A UREA SOLUTION FROM AMMONIA AND CARBON DIOXIDE

[75] Inventors: Andreas J. Biermans, Urmond; Kees Jonckers, Born, both of Netherlands

[73] Assignee: Unie Van Kunstmestfabrieken, B.V., Utrecht, Netherlands

[21] Appl. No.: 847,653

[22] Filed: Nov. 1, 1977

[30] Foreign Application Priority Data

Nov. 3, 1976 [NL] Netherlands .................. 7612162

[51] Int. Cl.$^2$ ......................................... C07C 126/02
[52] U.S. Cl. ............................................. 260/555 A
[58] Field of Search ................................... 260/555 A

[56] References Cited

U.S. PATENT DOCUMENTS

| 3,107,149 | 10/1963 | Wentworth et al. | 260/555 A |
|---|---|---|---|
| 3,867,442 | 2/1975 | Logemann | 260/555 A |

Primary Examiner—O. R. Vertiz
Assistant Examiner—Thomas W. Roy
Attorney, Agent, or Firm—Cushman, Darby & Cushman

[57] ABSTRACT

An improved process for the preparation of urea from carbon dioxide and ammonia at elevated temperature and pressure whereby unconverted ammonia, substantially free of carbon dioxide and water is recovered from a urea and ammonium carbamate containing liquid process stream. An urea and ammonium carbamate containing process stream is expanded to a pressure of between about 1 and 25 kg/cm$^2$ absolute and heated, thereby decomposing ammonium carbamate and forming a gas mixture containing ammonia, carbon dioxide and water vapor. The improvement comprises the steps of (a) introducing this gas mixture into a carbon dioxide separation column along with sufficient diluting water to form a first residual liquid phase, containing ammonia, carbon dioxide and from about 65 to 96 percent by weight water, in the bottom of such column, and separately removing therefrom an off-gas of carbon dioxide substantially free of ammonia, and the first residual liquid phase; (b) introducing this first residual liquid phase into a desorption column wherefrom a second off-gas containing ammonia, carbon dioxide and water vapor, is removed; (c) introducing the second off-gas into an ammonia separation column and separately removing therefrom a third off-gas of ammonia substantially free of carbon dioxide and water vapor, and a liquid phase containing ammonia, carbon dioxide and water; and (d) recycling the third gas phase back to the urea synthesis zone. The carbon dioxide separation column, desorption column and ammonia separation column are all operated at substantially the same pressure of between about 1 and 25 kg/cm$^2$ absolute.

6 Claims, 1 Drawing Figure

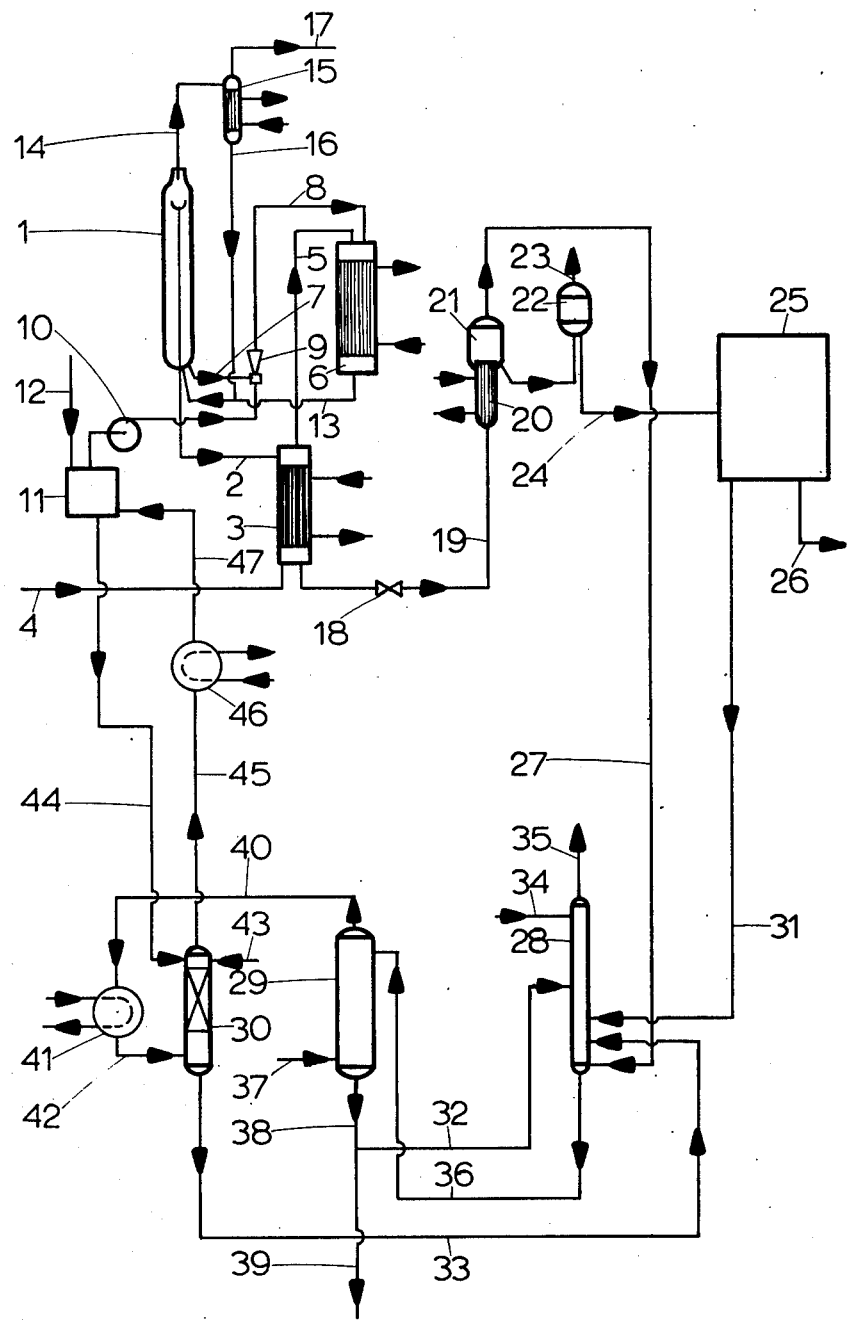

PROCESS FOR PREPARING A UREA SOLUTION FROM AMMONIA AND CARBON DIOXIDE

BACKGROUND OF THE INVENTION

If ammonia and carbon dioxide are reacted in a urea synthesis zone at elevated pressure and temperature suitable for the formation of urea, the reaction proceeds first to the formation of ammonium carbamate, and then, with a split-off of water, this ammonium carbamate is partly converted into urea. The aqueous urea solution leaving the urea synthesis zone thus contains nonconverted ammonium carbamate. Furthermore, if an excess of ammonia is introduced into the urea synthesis reactor, as is normally done, this aqueous urea solution will also contain free unreacted ammonia.

This urea and ammonium carbamate containing process stream is fed from the urea synthesis zone to one or more ammonium carbamate decomposition zones wherein, through a combination of process steps which may include expansion, heating and/or stripping, the ammonium carbamate is decomposed and the resulting ammonia and carbon dioxide, along with any free ammonia initially present in the process stream, is removed leaving an aqueous solution of urea. In most commercial processes, the gas mixture of ammonia, carbon dioxide and water vapor separated from the aqueous urea solution is absorbed and/or condensed and returned to the urea synthesis zone as an aqueous solution of ammonium carbamate. However, the drawback of this procedure is that water is introduced into the urea synthesis reactor where it impedes the conversion of ammonium carbamate into urea. This, in turn, results in a higher concentration of ammonium carbamate leaving the urea synthesis zone and therefore a higher energy consumption to decompose the ammonium carbamate and separate it from the aqueous urea solution. Earlier processes have been successful, through a combination of expansion and heating steps, in minimizing the quantity of water recycled with the aqueous ammonium carbamate solution. However, in such an aqueous solution recycle process some water must necessarily be present to maintain the ammonium carbamate in solution.

Other processes have proposed recycling the ammonium carbamate as a solid slurry of ammonium carbamate in an inert oil, or as a hot gas mixture of ammonia and carbon dioxide. In the oil slurry processes, additional equipment is required to form the slurry and to separate the oil from the finished product. In the hot gas process, enormous quantities of energy must be expended to compress the gas mixture, which must be maintained at an elevated temperature in order to prevent the deposition of solid ammonium carbamate. Neither of these proposals have gained significant commercial acceptance.

It has also been proposed to separately compress and recycle the ammonia and/or carbon dioxide to avoid the formation of solid ammonium carbamate. However, mixtures of ammonia and carbon dioxide form a maximum boiling azeotrope and therefore resist separation by conventional means. Therefore, it has been proposed, for example in German Pat. Spec. No. 669,314, to separate the ammonia and carbon dioxide from the gas mixture resulting from the decomposition of ammonium carbamate by selective absorption of carbon dioxide in, for example, a monoethanolamine solution. However, this has the disadvantage that the absorbed carbon dioxide must thereafter be removed from the absorption agent by heating.

It has further been proposed to absorb the gaseous mixture of ammonia and carbon dioxide in water or an aqueous solution, thereafter remove free ammonia from the solution by distillation at atmospheric pressure and subsequently separately remove carbon dioxide by fractional distillation at a higher pressure of from between 5 to 20 atmospheres. A process of this type is disclosed in British Pat. Specification No. 1,129,939. However, the drawback of processes of this type is that it is first necessary to expand the gas mixture to atmospheric pressure and thereafter bring the remaining solution up to a pressure of 5 to 20 atmospheres after the ammonia has been removed. Moreover, the ammonia is obtained at atmospheric pressure and if it is to be returned to the urea synthesis zone, energy must be expended to compress it up to the urea synthesis pressure.

BRIEF SUMMARY OF INVENTION

A process has now been found whereby the decomposition of nonconverted carbamate and the recycle of the ammonia and/or carbon dioxide obtained thereby can be carried out in a simpler manner, achieving a substantial decrease in the consumption of energy along with a significant saving of capital investment cost.

This is accomplished, according to the invention, by treating a gas mixture containing ammonia, carbon dioxide and water vapor derived from the decomposition of ammonium carbamate, in a series of process steps to separately obtain ammonia substantially free of carbon dioxide and water, and carbon dioxide substantially free of ammonia. This gas mixture is obtained from an ammonium carbamate decomposition zone wherein a urea containing liquid process stream, also containing unconverted ammonium carbamate, is expanded to a pressure of between about 1 to 25 kg/cm$^2$ absolute and heated, thereby decomposing at least a portion of the ammonium carbamate.

This gas mixture is separated from the urea containing liquid process stream and introduced into a carbon dioxide separation column, together with sufficient diluting water to form, in the bottom of such column, a first residual liquid phase containing ammonia, carbon dioxide and between about 65 and 96 percent by weight water. Preferably sufficient diluting water is added to achieve a water content of between about 80 and 95 percent by weight in this first residual liquid phase.

A first off-gas of carbon dioxide substantially free of ammonia, and this first residual liquid phase are separately removed from the carbon dioxide separation column, and the carbon dioxide can be discarded, compressed and recycled to the urea synthesis zone, or used elsewhere.

The first residual liquid phase is introduced into a desorption column wherein substantially all of the ammonia and carbon dioxide are removed from the liquid phase. The resulting second off-gas, containing ammonia, carbon dioxide and water varpor, and second residual liquid phase, containing water substantially free of ammonia and carbon dioxide, are separately removed from the desorption column. This second residual liquid phase can be discarded or used as diluting water in the carbon dioxide separation column.

The second off-gas is introduced into an ammonia separation column and a third off-gas of ammonia substantially free of carbon dioxide and water vapor, and a third residual liquid phase containing ammonia, carbon dioxide and water, are separately removed therefrom. This third off-gas of ammonia is condensed and recycled to the urea synthesis zone. The third residual liquid phase may, if desired, be introduced into the carbon dioxide separation column wherein its water content constitutes a portion of the diluting water.

In this process, the ammonia separation column, desorber and carbon dioxide separation column are all operated at substantially the same pressure, which pressure should be between about 1 and 25 kg/cm$^2$ absolute, and preferably between about 1 and 6 kg/cm$^2$ absolute.

BRIEF DESCRIPTION OF THE DRAWING

The drawing illustrates the invention specifically as applied to a urea process wherein the urea synthesis effluent is first subjected to a stripping treatment, and the resulting urea containing liquid process stream, also containing ammonium carbamate, is expanded and heated to produce the gas mixture treated in accordance with the invention. Such a stripping process is described, for example, in U.S. Pat. No. 3,867,442. However, it should be understood that the invention can also advantageously be applied to other urea processes having a urea and ammonium carbamate containing liquid process stream under pressure, which can be expanded to a pressure of between about 1 and 25 kg/cm$^2$ absolute and heated to produce a gas mixture which can be treated in accordance with the invention.

DETAILED DESCRIPTION OF THE DRAWING

In the urea reactor 1 a urea synthesis solution is formed at a pressure of between about 110 and 250 kg/cm$^2$ and a temperature of between about 165° and 220° C. This solution is supplied, via line 2, to stripper 3, which can operate at synthesis pressure or at a lower pressure, and is therein countercurrently contacted under heating, with fresh carbon dioxide, or possibly ammonia or a combination of the two, supplied via line 4. The gas mixture consisting of ammonia, carbon dioxide and water expelled from the stripper is fed via line 5 into a condenser 6, which preferably operates at synthesis pressure. A portion of the solution formed in the bottom part of the urea reactor 1 is also supplied to condenser 6 via lines 7 and 8 with the aid of ejector 9 to raise the condensation temperature, so that the heat of condensation is obtained at as high as possible a temperature level. With the aid of this heat, steam of 1–6 kg/cm$^2$ absolute is produced, which can be used elsewhere in the process. The ejector 9 is driven with the aid of ammonia, which is supplied from storage tank 11 via pump 10. Fresh ammonia is supplied via line 12. In condenser 6 full or partial condensation and and absorption of the gas mixture supplied via line 5 takes place. The ammonium carbamate solution so obtained together with the uncondensed portion of the gas mixture, of any, are fed into urea reactor 1 via line 13 along with the carbamate solution which has been obtained by condensation of ammonia, carbon dioxide and water from a gas mixture which is discharged via line 14 from the top of the urea reactor 1. Such gas mixture also contains any inert components that may have been contained in the fresh carbon dioxide or ammonia and, possibly air or oxygen which may have been used for passivation of equipment and lines. This condensation takes place in purge gas condenser 15, which is connected by means of line 16 to line 13 or to the lower part of urea reactor 1. The gas mixture not condensed in the purge gas condenser is eventually fed via line 17 to an absorber (not shown) operating at a lower pressure, in order to recover the ammonia still present.

The stripped urea synthesis solution is discharged from stripper 3 and, after expansion to a pressure of 2–5 kg/cm$^2$ in reducer valve 18, fed through line 19 into carbamate decomposer 20. In carbamate decomposer 20, the carbamate still present is all but fully decomposed by heating. The gas mixture leaving the heating zone of carbamate decomposer 20, along with the urea solution, is separated from the solution in separator 21 and next fed to an installation for separation of ammonia, carbon dioxide, and water to be discussed in more detail below. The aqueous urea solution obtained in the separator 21 of carbamate decomposer 20 is expanded in expansion vessel 22 to atmospheric pressure, in which some more dissolved ammonia and water vapor escape and are discharged via line 23. Via line 24, the aqueous urea solution is fed to sections indicated as a whole by 25, wherein it is concentrated in a known manner by evaporation or crystallization, or may be processed in some other known way. The end product is discharged via 26.

The gas mixture separated from the urea solution in separator 21 is fed, via line 27, to an installation for separation of ammonia, carbon dioxide and water, which installation mainly comprises carbon dioxide separation column 28, a desorption column 29, and an ammonia separation column 30. These columns all operate at substantially the same pressure, which lies between about 1 and 25 kg/cm$^2$ absolute. An additional advantage can be obtained if the separation system is operated at a pressure of between about 1 and 6 kg/cm$^2$ absolute, because in that case the pressure can be essentially the same as the pressure at which the gas mixture is separated in separator 21 and the steam formed in condenser 6 can be utilized in desorption column 29.

In the bottom part of column 28 the gas mixture is contacted with such an amount of water that virtually all ammonia and water is absorbed or condensed and that carbon dioxide containing only very little ammonia and water ascends to the top part of the column. To this end, water or an aqueous solution, e.g., process condensate from section 25, is supplied via line 31, and, aqueous solutions from subsequent separation stages are recycled via lines 32 and 33. In the top part of column 28 the ascending gas mixture is washed with water supplied via line 34, in order to remove the minor amounts of ammonia still present in it. This water, with the absorbed ammonia, also enters the bottom part of the column. The total weight-quantity of water suppllied to the bottom part of column 28 via lines 31, 32, 33 and 34 is such that the solution discharged from the bottom of the column contains from about 65 to 96 percent by weight water, i.e., an amount 5 to 20 times the weight-quantity of the gas mixture supplied via line 27. As a rule, the optimum water content is from 80 to 95 percent by weight and accordingly the weight-quantity of water to be added is preferably from 8 to 15 times the weight-quantity of gas-mixture. By operating the column in this manner the removal of carbon dioxide and ammonia from the gas mixture separated in separator 21 is effected at an attractively low total energy consumption in the separation section. The temperature in the bottom part of the column lies between about 70° and 190° C. and in the top part of the column a temperature of between about 30° and 70° C. is maintained.

From the top of column 28, carbon dioxide is discharged, via line 35, which contains only a few percent of water and, at the most, traces of ammonia. This gas is purged. The bottom product of column 28 contains substantially all of the ammonia which was present in the gas mixture supplied via line 27, any carbon dioxide not separated and purged from the column, and water. This solution is fed via line 36 into desorption column 29, in which virtually all ammonia and carbon dioxide are desorbed with the aid of, for example, direct steam supplied via line 37. The bottom product of desorption column 29 is water substantially free of ammonia and carbon dioxide, preferably below the limits permitted by environmental control regulations, and is discharged via line 38. Part of this bottom product may be led into carbon dioxide separation column 28 via line 34 as diluting or washing water. The remaining portion is discharged via line 39 and may be fully or partly returned to section 26.

Desorption column 29 is operated with a top temperature of between about 105° and 175° C. The top product of the desorption column 29 contains, in addition to carbon dioxide and water, substantially all of the ammonia separated off in separator 21 and also a quantity of circulating ammonia. This top product is led into ammonia separation column 30 via line 40, cooler 41, and line 42, in which column, with the aid of water supplied via line 43 and liquid ammonia supplied via line 44, the carbon dioxide and the water are removed. The ammonia thus obtained, which is substantially free of carbon dioxide and water is sent via line 45 to cooler 46, in which it is condensed. The thus condensed liquid ammonia is fed via line 47 to ammonia storage tank 11. The bottom solution formed in the ammonia sepration column, consisting of ammonia, carbon dioxide and water, is recycled to carbon dioxide separation column 28 via line 33.

The carbon dioxide separation column 28 and ammonia separation column 30 may be any type of column appropriate for the separation of gaseous and liquid components in accordance with the invention, including but not limited to rectification, washing and distillation columns.

In the process described above essentially no water is returned to the urea synthesis from the low-pressure stage, i.e., the part of the process after reducer valve 18. As a result of this an appreciably higher degree of conversion is achieved in the urea reactor, so that a synthesis solution containing less carbamate is obtained. Because less carbamate has to be decomposed in the stripper, and the stripping runs more effectively because of the lower water content, a smaller amount of steam is necessary in the stripper. The consumption of steam for the ammonia/carbon dioxide/water separation is more than compensated by a decrease of the amount of steam in the processing of the urea solution because the quantity of water to be evaporated is smaller. Since no solution is recycled from the low-pressure stage, but only gaseous ammonia, the operation of the installation is easier. The operational reliability is enlarged because the traditionally vulnerable carbamate pumps are no longer necessary.

EXAMPLE

The urea synthesis and stripping portion of the installation as described above is fed with a fresh feed of 2317 kmole/hr of ammonia via line 12, and 1142 kmole/hr of carbon dioxide via line 4, resulting in 1019 kmole/hr of urea, leaving the bottom of stripper 3 in the form of an aqueous solution. A pressure of about 140 kg/cm$^2$ is maintained in urea reactor 1, stripper 3, condenser 6, and purge-gas condenser 15.

In urea reactor 1, a synthesis solution is formed at an average temperature of 183° C. containing 1061 kmole/hr urea, 2683 kmole/hr ammonia, 627 kmole/hr carbon dioxide and 1191 kmole/hr water. The $CO_2$ conversion in this solution, therefore, amounted to 62,8%.

In stripper 3, the synthesis solution discharged from urea reactor 1 is stripped with a fresh carbon dioxide stripping gas fed via line 4 with the aid of 215° C. steam, resulting in 2542 kmole/hr of ammonia, 551 kmole/hr carbon dioxide and 132 kmole/hr water being expelled from this synthesis solution.

The gas mixture discharged from stripper 3 via line 5 is partially condensed in condenser 6 with the aid of a mixture, supplied via line 8, of fresh ammonia and synthesis solution aspirated from the urea reactor via line 7. The gas-liquid mixture thus formed in condenser 6, together with the carbamate solution formed in the purge gas condenser 15, (consisting of 497 kmole/hr ammonia, 169 kmole/hr of carbon dioxide and 33 kmole/hr of water) are returned to the urea reactor.

A solution consisting of 1019 kmole/hr of urea, 225 kmole/hr of ammonia, 118 kmole/hr of carbon dioxide and 1019 kmole/hr of water is discharged from stripper 3, which solution is expanded to 2.5 kg/cm$^2$ and thereafter heated to 124° C. in carbamate decomposer 20. A gas mixture consisting of 151 kmole/hr of ammonia, 98 kmole/hr of carbon dioxide and 159 kmole/hr of water is formed, and is separated in separator 21 from the remaining urea solution. The remaining urea solution, in addition to 1019 kmole/hr of urea and 860 kmole/hr of water, still contains 74 kmole/hr of ammonia and 20 kmole/hr of carbon dioxide. This remaining ammonia and carbon dioxide is substantially all removed in expansion vessel 22, so that an aqueous urea solution is obtained.

The gas mixture separated in separator 21 is fed into the bottom of carbon dioxide separation column 28, and is there mixed with process condensate from the final processing section, which contains 1117 kmole/hr of water, 5.5 kmole/hr of ammonia and 2.25 kmole/hr of carbon dioxide and has a temperature of 90° C. Column 28 is also supplied via line 32 with 3700 kmole/hr of water which contains traces of ammonia, via line 33 with a solution containing 739 kmole/hr of water, 298 kmole/hr of ammonia and 135 kmole/hr of carbon dioxide, and via line 34 with 157 kmole/hr of water. The temperature of the solution supplied via lines 32 and 33 is 88° C. and 85° C. respectively, and the temperature of the water supplied via line 34 is 40° C.

The gas mixture escaping from the top of column 28 consists of 143 kmole/hr of carbon dioxide and 3 kmole/hr of water. The bottom solution from column 28, which has a temperature of 106° C. and consists of 5939 kmole/hr of water, 461 kmole/hr of ammonia and 92 kmole/hr of carbon dioxide, is led to desorption column 29.

To this desorption column 29, is also supplied a gas mixture recovered from the top product of purge-gas condenser 15 and consisting 156.5 kmole/hr of ammonia, 39.2 kmole/hr of carbon dioxide and 371 kmole/hr of water. Steam at a temperature of 138° C. is also fed into the bottom part of desorption column 29.

The bottom product of this desorption column 29 consists of 6972 kmole/hr of water, in which there are still traces of ammonia and carbon dioxide. A part of this water is supplied via lines 32 and 34 to carbon dioxide separation column 28, another part is used as washing water in the ammonia separation column 30 via line 43, and the remainder is used elsewhere in the process or is discharged to the sewer.

The gas mixture discharged from the top of the desorption column 29 has a temperature of of 110° C. and consists of 617 kmole/hr of ammonia, 134 kmole/hr of carbon dioxide and 709 kmole/hr of water. After cooling to 87° C. in cooler 41, this gas mixture is introduced into ammonia separation column 30 and therein washed with 29 kmole/hr of water at 40° C. and 170 kmole/hr of ammonia at −15° C. The resulting gaseous product discharged from the top of column 30 consists of 490 kmole/hr of substantially pure ammonia suitable for recyle to the urea reactor.

What is claimed is:

1. In a process for the preparation of urea from ammonia and carbon dioxide in a urea synthesis zone at an elevated temperature and pressure, having at least one ammonium carbamate decomposition zone wherein a urea containing liquid process stream, also containing unconverted ammonium carbamate, is expanded to a pressure of between about 1 and 25 kg/cm$^2$ absolute and heated thereby decomposing at least a portion of said ammonium carbamate and yielding a gas mixture containing ammonia, carbon dioxide and water vapor, the improvement comprising the steps of introducing said gas mixture into a carbon dioxide separation column, along with sufficient diluting water to form, in the bottom of said column, a first residual liquid phase containing ammonia, carbon dioxide and between about 65 and 96 percent by weight water, and separately removing therefrom a first off-gas of carbon dioxide substantially free of ammonia, and said first residual liquid phase, introducing said first residual liquid phase into a desorption column and separately removing therefrom a second off-gas containing ammonia, carbon dioxide and water vapor, and a second residual liquid phase containing water substantially free of ammonia and carbon dioxide, introducing said second off-gas into an ammonia separation column and separately removing therefrom a third off-gas of ammonia substantially free of carbon dioxide and water vapor and a third residual liquid phase containing ammonia, carbon dioxide and water, and recycling said third off-gas to said urea synthesis zone, and introducing said third residual liquid phase into said carbon dioxide separation column, the water content of such third residual liquid phase constituting a portion of said diluting water, wherein said ammonia separation column, desorption column and carbon dioxide separation column are all operated at substantially the same pressure of between about 1 and 25 kg/cm$^2$ absolute.

2. The process of claim 1 wherein said ammonia separation column, desorption column and carbon dioxide separation column are all operated at substantially the same pressure of between about 1 and 6 kg/cm$^2$ absolute.

3. The process of claim 1 wherein sufficient diluting water is added to said carbon dioxide separation column so as to form a first residual liquid phase containing ammonia, carbon dioxide and between about 80 and 95 percent by weight water.

4. In a process for the preparation of urea from ammonia and carbon dioxide in a urea synthesis zone at an elevated temperature and pressure, having first and second ammonium carbamate decomposition zones wherein, in said first ammonium carbamate decomposition zone, a urea containing liquid process stream also containing unconverted ammonium carbamate, is heated and stripped by a countercurrent flow of gas selected from the group consisting of ammonia, carbon dioxide or a combination thereof, thereby decomposing a portion of said ammonium carbamate, and resulting in a first gas mixture containing ammonia, carbon dioxide and water vapor, which is thereafter at least partially condensed and recyled to said urea synthesis zone, and a residual urea containing liquid process stream, still containing ammonium carbamate, and in said second ammonium carbamate decomposition zone, said residual process stream is expanded to a pressure of between about 1 and 25 kg/cm$^2$ absolute and heated thereby further decomposing ammonium carbamate and yielding a second gas mixture containing ammonia, carbon dioxide and water vapor, the improvement comprising the steps of introducing said second gas mixture into a carbon dioxide separation column, along with sufficient diluting water to form, in the bottom of said column, a first residual liquid phase containing ammonia, carbon dioxide and between about 65 and 96 percent by weight water, and separately removing therefrom a first off-gas of carbon dioxide substantially free of ammonia, and said first residual liquid phase introducing said first residual liquid phase into a desorption column and separately removing therefrom a second off-gas containing ammonia, carbon dioxide and water vapor, and a second residual liquid phase containing water substantially free of ammonia and carbon dioxide, introducing said second off-gas into an ammonia separation column and separately removing therefrom a third off-gas of ammonia substantially free of carbon dioxide and water vapor and a third residual liquid phase containing ammonia, carbon dioxide and water, and recycling said third off-gas to said urea synthesis zone, and introducing said third residual liquid phase into said carbon dioxide separation column, the water content of such third residual liquid phase constituting a portion of said diluting water, wherein said ammonia separation column, desorption column and carbon dioxide separation column are all operated at substantially the same pressure of between about 1 and 25 kg/cm$^2$ absolute.

5. The process of claim 4 wherein said ammonia separation column, desorption column and carbon dioxide separation column are all operated at substantially the same pressure of between about 1 and 6 kg/cm$^2$ absolute.

6. The process of claim 4 wherein sufficient diluting water is added to said carbon dioxide separation column so as to form a first residual liquid phase containing ammonia, carbon dioxide and between about 80 and 95 percent by weight water.

* * * * *